United States Patent
Kim et al.

(10) Patent No.: US 9,887,644 B2
(45) Date of Patent: Feb. 6, 2018

(54) STRETCHABLE TRIBOELECTRIC GENERATOR, STRETCHABLE ELECTRICITY STORAGE DEVICE, AND WEARABLE ELECTRONIC DEVICE

(71) Applicant: Seoul National University R&DB Foundation, Seoul (KR)

(72) Inventors: Daehyeong Kim, Incheon (KR); Taeghwan Hyeon, Seoul (KR); Sungmook Jung, Gongju-si (KR); Seungki Hong, Seoul (KR); Jaemin Kim, Seoul (KR); Jongsu Lee, Seoul (KR)

(73) Assignee: SEOUL NATIONAL UNIVERSITY R&DB FOUNDATION (KR)

( * ) Notice: Subject to any disclaimer, the term of this patent is extended or adjusted under 35 U.S.C. 154(b) by 211 days.

(21) Appl. No.: 14/685,569

(22) Filed: Apr. 13, 2015

(65) Prior Publication Data
US 2016/0036351 A1    Feb. 4, 2016

(30) Foreign Application Priority Data

Jul. 30, 2014   (KR) .................. 10-2014-0097605
Feb. 27, 2015   (KR) .................. 10-2015-0028512

(51) Int. Cl.
*H02N 1/04* (2006.01)
*A61B 5/11* (2006.01)

(52) U.S. Cl.
CPC ............. *H02N 1/04* (2013.01); *A61B 5/1116* (2013.01)

(58) Field of Classification Search
CPC ........ H02N 1/04; G01P 15/125; A61B 5/1116
See application file for complete search history.

(56) References Cited

U.S. PATENT DOCUMENTS 3,091,069 A * 5/1963 Brasefield ................. C09C 1/60
                                                 23/314
3,201,620 A * 8/1965 Balientine ................. A61L 9/22
                                                 310/310
3,206,624 A * 9/1965 Cotter ....................... G01K 7/06
                                                 310/306

(Continued)

FOREIGN PATENT DOCUMENTS

KR      20130126796         11/2013
WO    WO 2015137532 A1  *  9/2015    ............... H02N 1/04

OTHER PUBLICATIONS

Yuan, Longyan et al., "Flexible Solid-State Supercapacitors Based on Carbon Nanoparticles/MnO2 Nanorods Hybrid Structure," American Chemical Society, published online Dec. 19, 2011, www.acsnano.org, ACSNANO 2012, vol. 6, No. 1, pp. 656-661.

*Primary Examiner* — David Bolduc
(74) *Attorney, Agent, or Firm* — Renaissance IP Law Group LLP

(57) ABSTRACT

Disclosed herein are a stretchable triboelectric generator, a stretchable electricity storage device and a wearable electronic device. The stretchable triboelectric generator comprises a first stretchable triboelectric generation part comprising a first fabric layer and a first friction layer on the first fabric layer and a second stretchable triboelectric generation part comprising a second fabric layer and a second friction layer on the second fabric layer. The stretchable electricity storage device comprises at least one of a stretchable battery or a stretchable supercapacitor. The stretchable electricity storage device may be connected to the stretchable triboelectric generator and may store electricity generated by the stretchable triboelectric generator. The wearable electronic device comprises the stretchable triboelectric generator, the stretchable electricity storage device and a sensor connected electrically to at least one of the stretchable triboelectric generator or the stretchable electricity storage device to sense vital signs, bio signals, or body's movement changes.

8 Claims, 16 Drawing Sheets

(56) References Cited

U.S. PATENT DOCUMENTS

| | | | | |
|---|---|---|---|---|
| 4,126,822 A * | 11/1978 | Wahlstrom | ............ | G04C 10/00 310/309 |
| 4,990,813 A * | 2/1991 | Paramo | ............ | H02N 1/04 310/308 |
| 8,187,795 B2 * | 5/2012 | Jain | ............ | B81C 1/0019 257/E23.117 |
| 8,283,739 B2 * | 10/2012 | Park | ............ | B82Y 10/00 257/415 |
| 2006/0280322 A1 * | 12/2006 | Abe | ............ | H01R 13/24 381/300 |
| 2008/0138602 A1 * | 6/2008 | Canham | ............ | A61B 17/06166 428/311.11 |
| 2009/0027828 A1 * | 1/2009 | Jung | ............ | H01G 9/0032 361/502 |
| 2010/0253184 A1 * | 10/2010 | Choi | ............ | H02N 2/18 310/339 |
| 2011/0050181 A1 * | 3/2011 | Post | ............ | H02N 1/04 320/166 |
| 2013/0020909 A1 * | 1/2013 | Kim | ............ | H02N 2/18 310/339 |
| 2013/0049531 A1 * | 2/2013 | Wang | ............ | H02N 1/04 310/309 |
| 2014/0029164 A1 * | 1/2014 | Park | ............ | H01G 11/36 361/502 |
| 2014/0131868 A1 * | 5/2014 | Kippelen | ............ | H01B 1/24 257/741 |
| 2014/0202517 A1 * | 7/2014 | Kippelen | ............ | H01L 51/004 136/244 |
| 2015/0061460 A1 * | 3/2015 | Bae | ............ | H02N 1/04 310/310 |
| 2015/0144899 A1 * | 5/2015 | Verilhac | ............ | H01L 51/0023 257/40 |
| 2015/0311823 A1 * | 10/2015 | Wang | ............ | H02N 1/04 310/300 |
| 2015/0361223 A1 * | 12/2015 | Woo | ............ | C08G 61/126 136/263 |
| 2016/0156282 A1 * | 6/2016 | Kim | ............ | H02N 1/04 607/61 |

* cited by examiner

[FIG. 1]
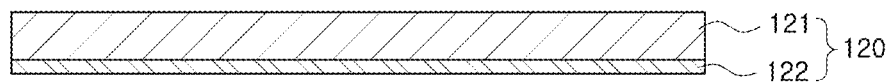
[FIG. 2A]
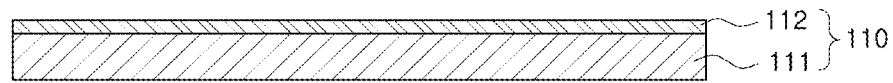
[FIG. 2B]
[FIG. 3]
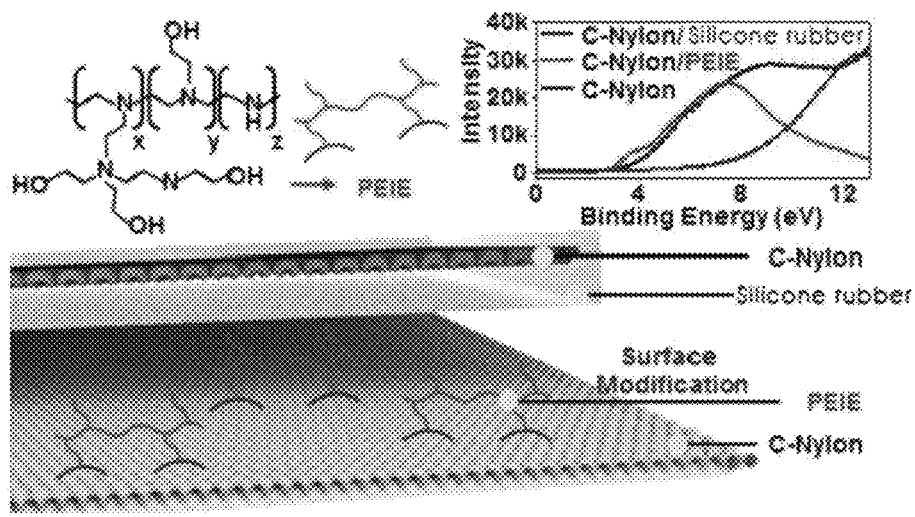

[FIG. 4]
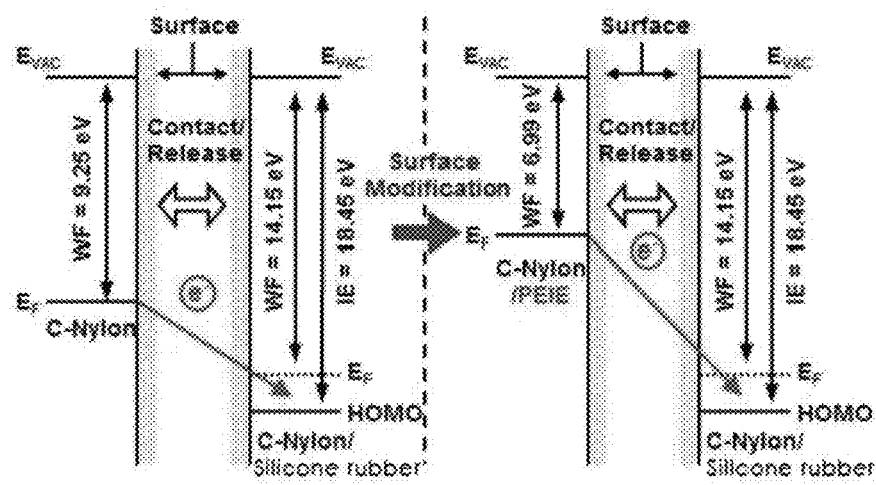
[FIG. 5A]
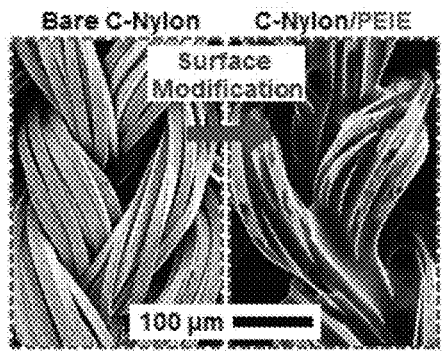
[FIG. 5B]
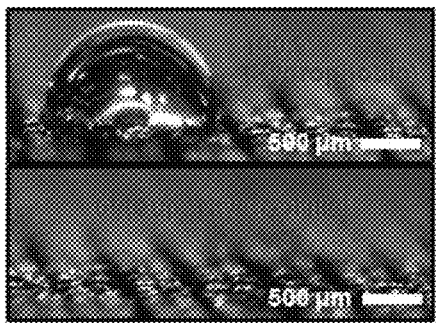

[FIG. 6A]
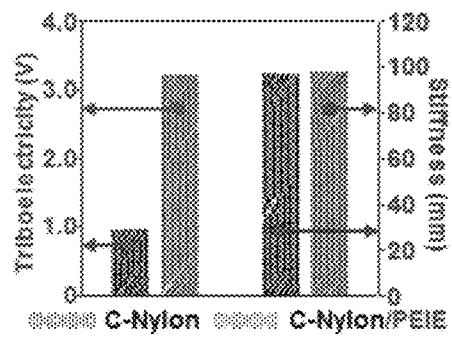
[FIG. 6B]
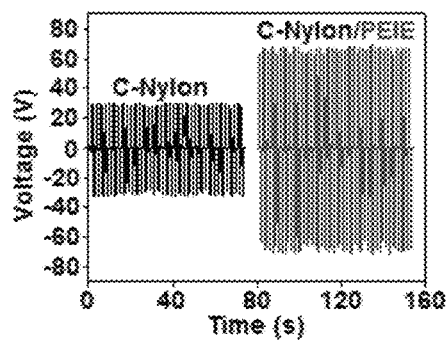
[FIG. 6C]
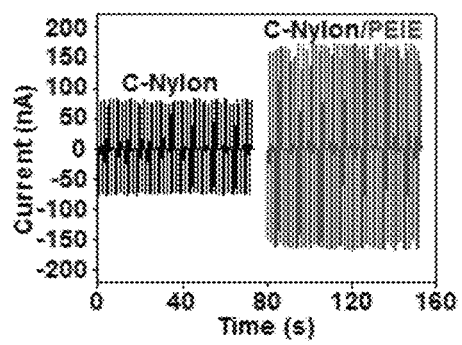

[FIG. 6D]
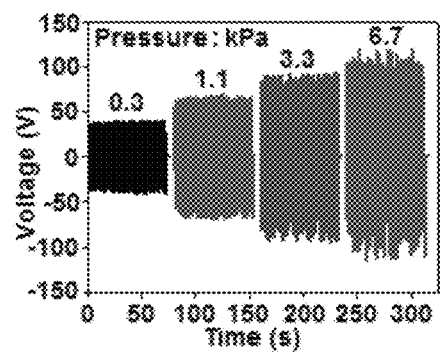
[FIG. 6E]
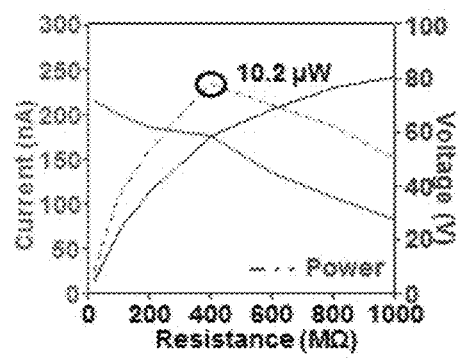
[FIG. 7]
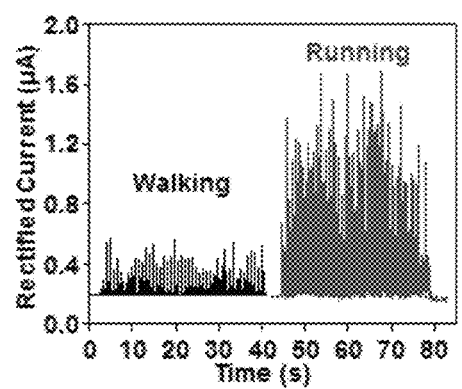

[FIG. 8]
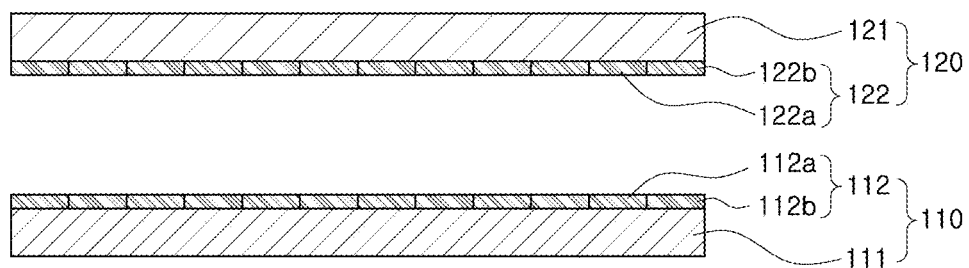
[FIG. 9A]
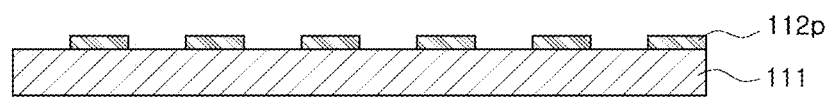
[FIG. 9B]
[FIG. 9C]
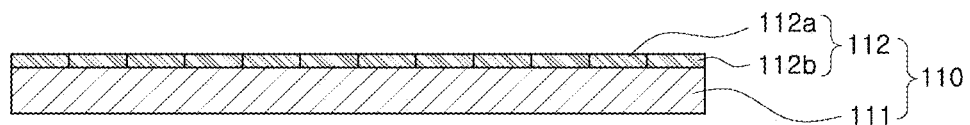
[FIG. 9D]
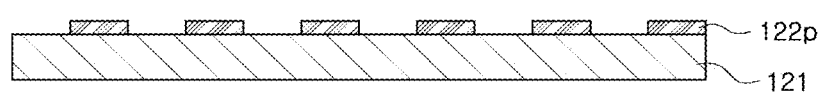

[FIG. 9E]
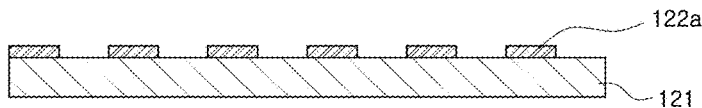
[FIG. 9F]
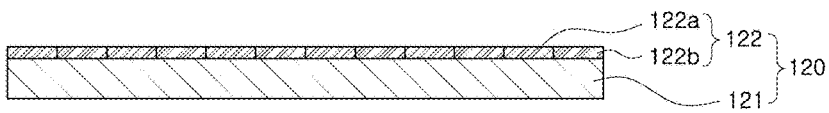
[FIG. 10]
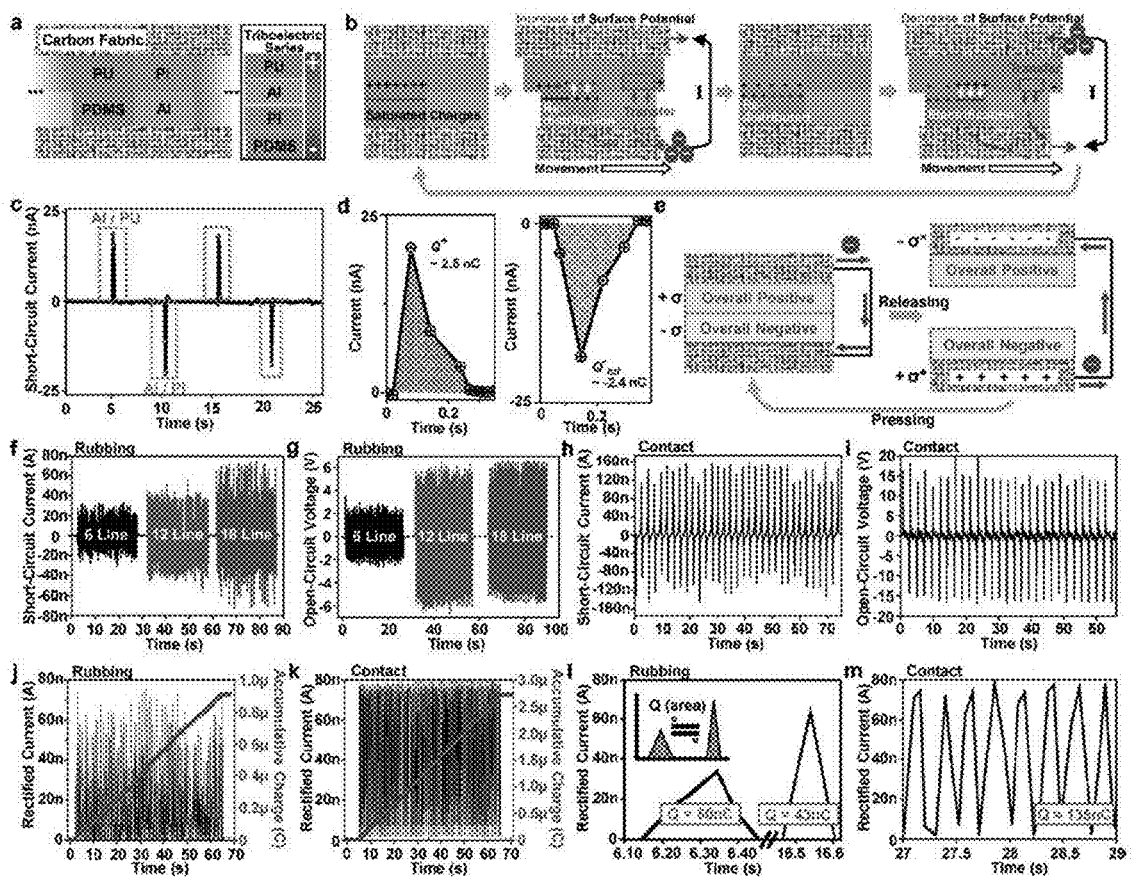

[FIG. 11]
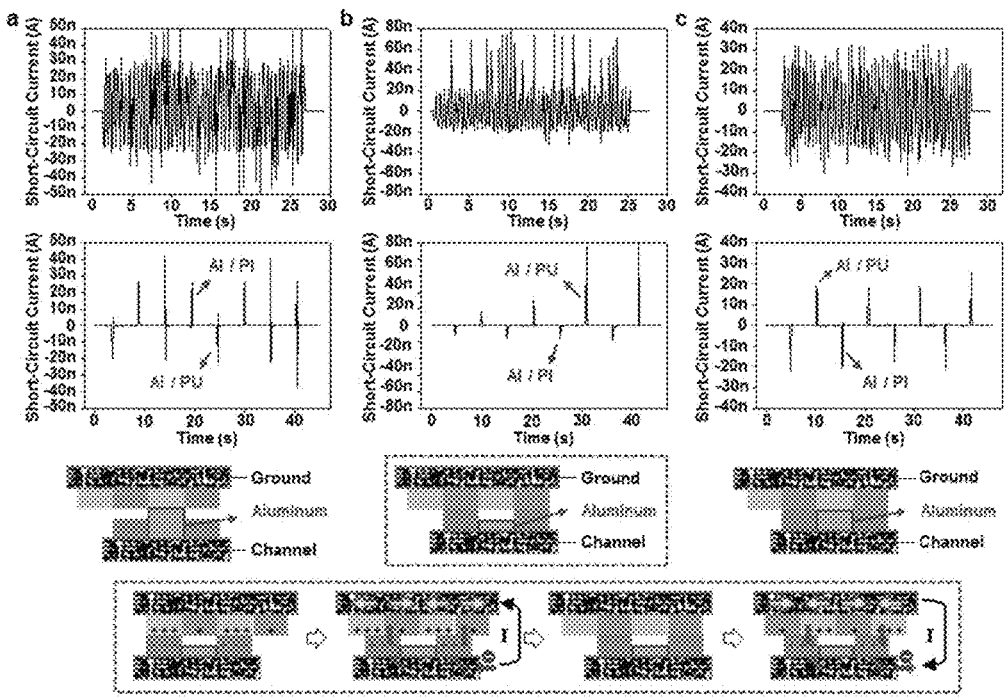
[FIG. 12]
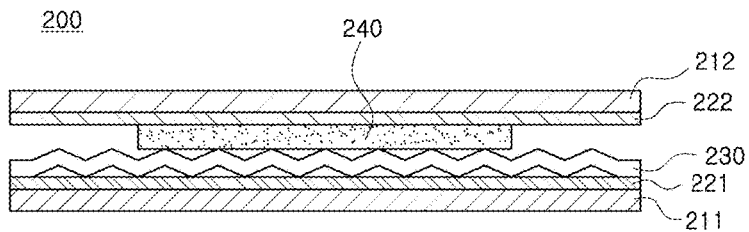
[FIG. 13A]
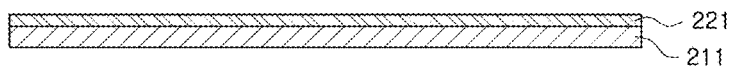

[FIG. 13B]
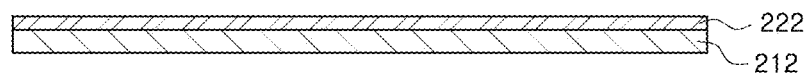
[FIG. 13C]
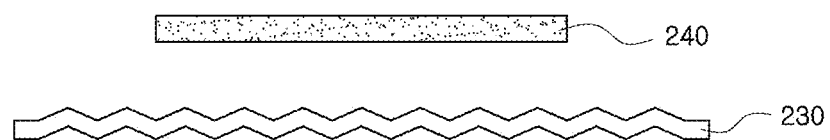
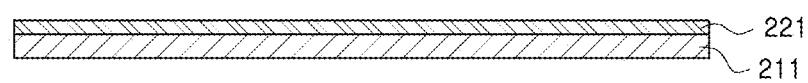
[FIG. 14]
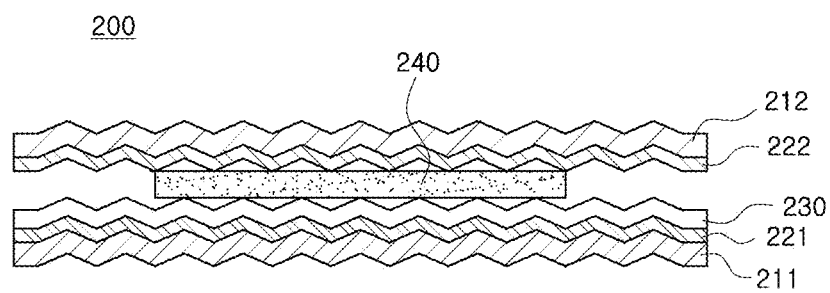

[FIG. 15]
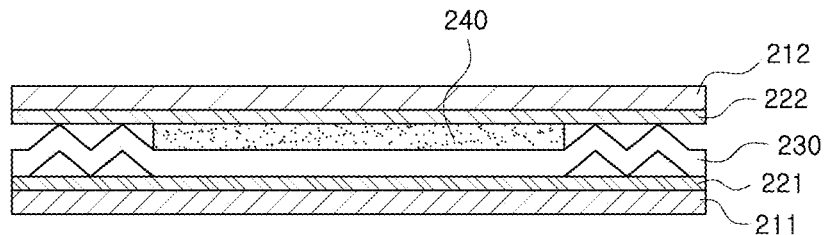
[FIG. 16]
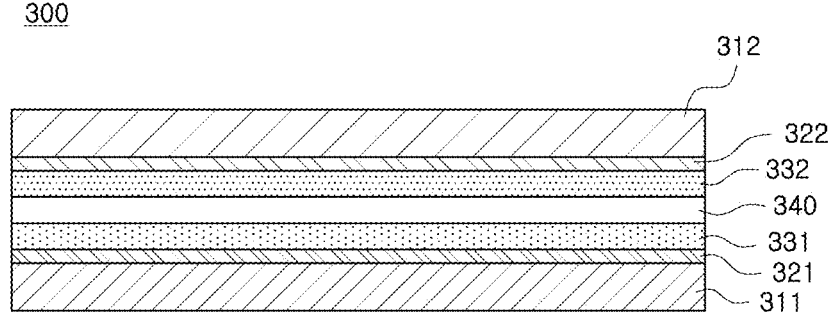
[FIG. 17A]
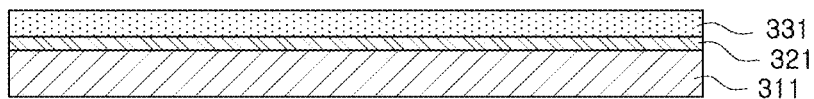
[FIG. 17B]
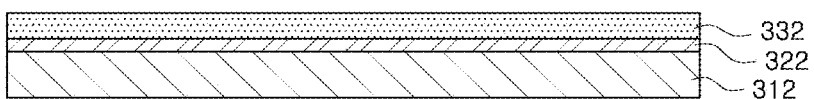

[FIG. 17C]
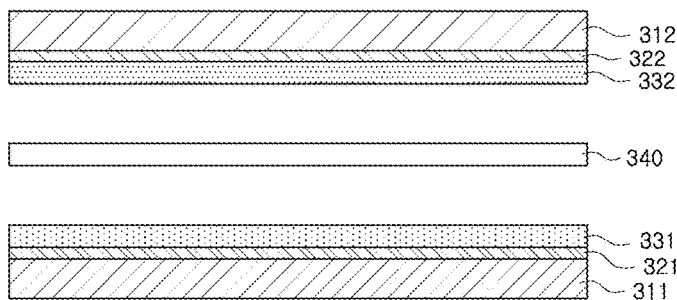
[FIG. 18]
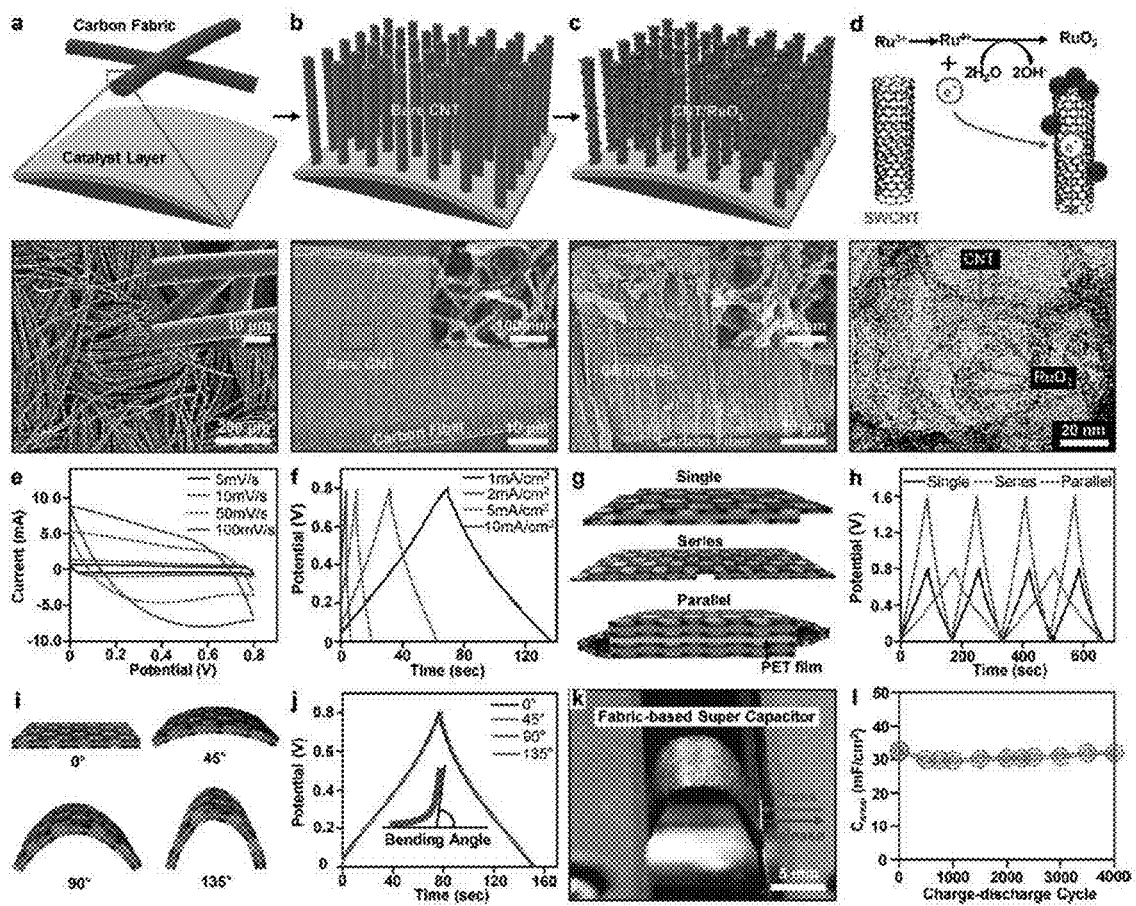

[FIG. 19A]
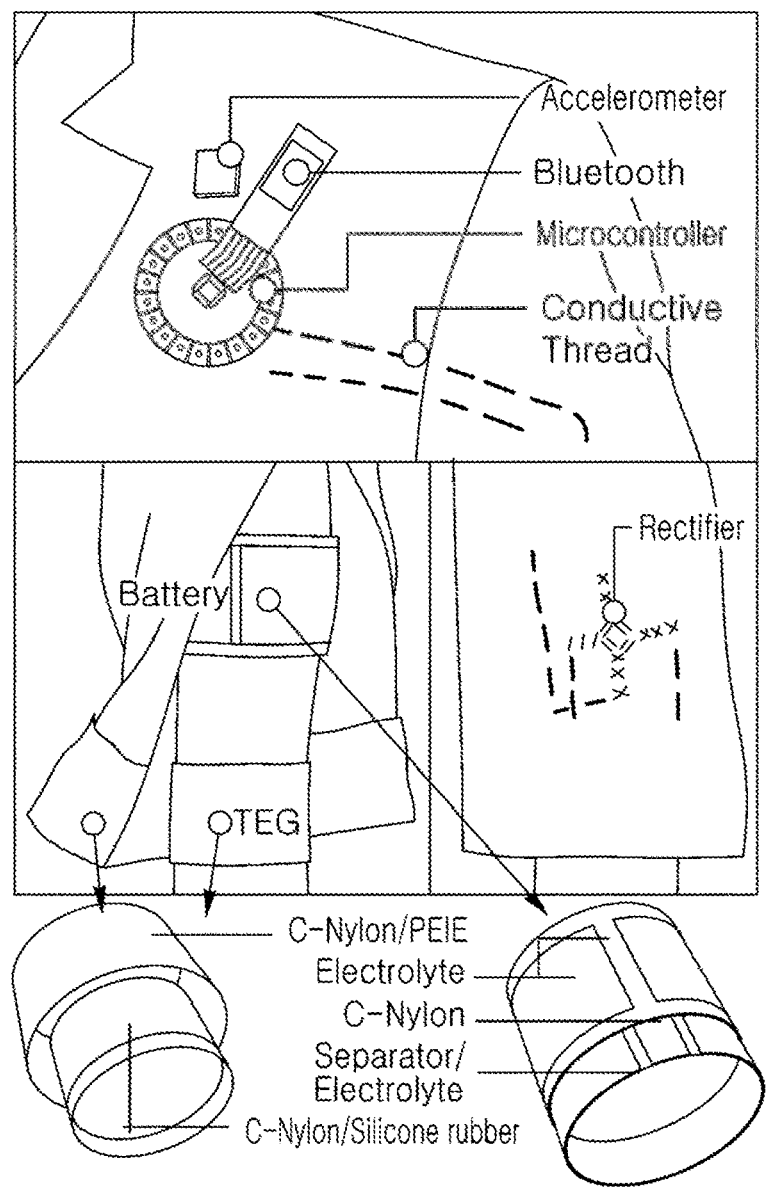

[FIG. 19B]
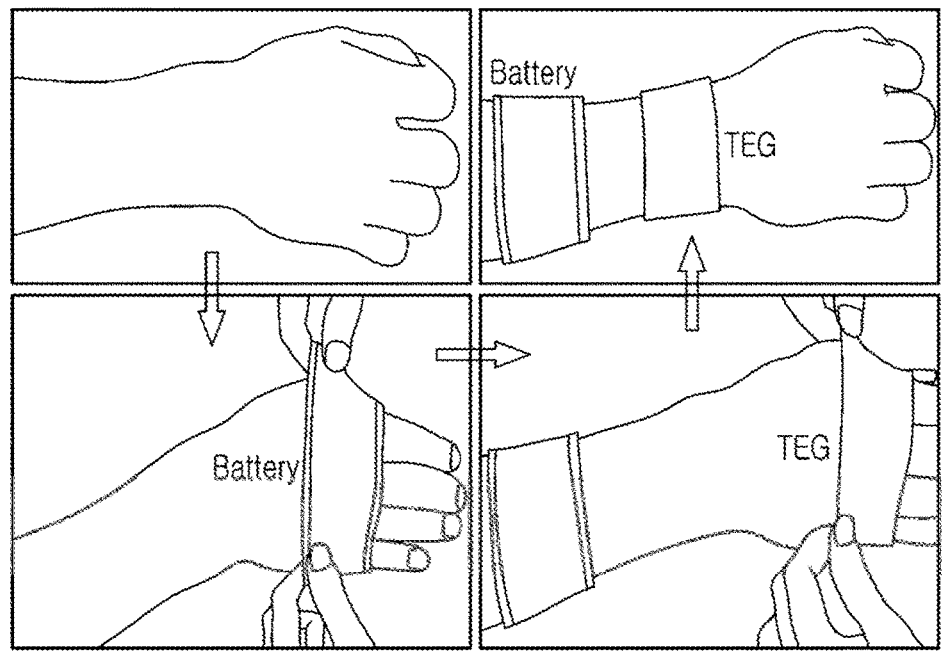
[FIG. 19C]
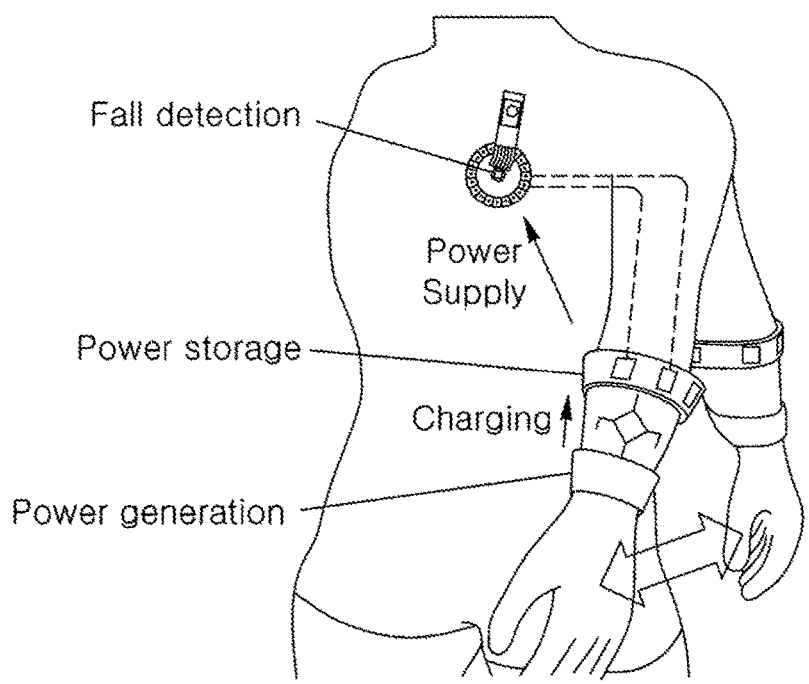

[FIG. 19D]
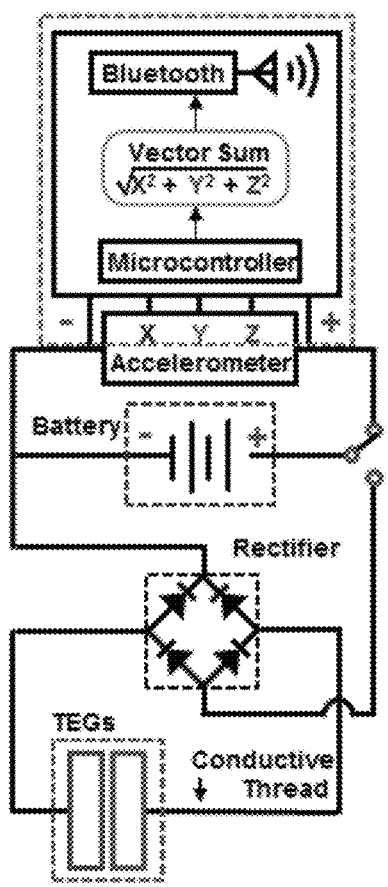
[FIG. 19E]
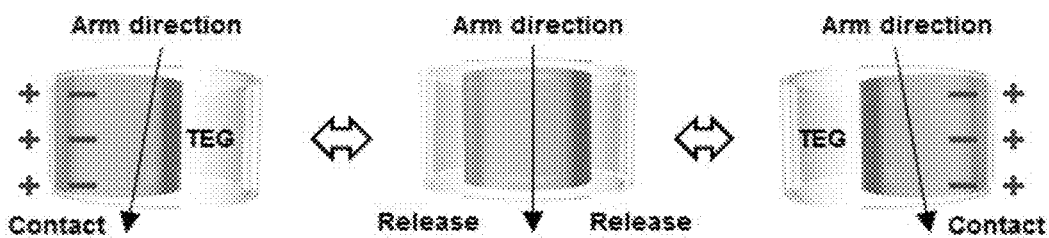

[FIG. 20A]
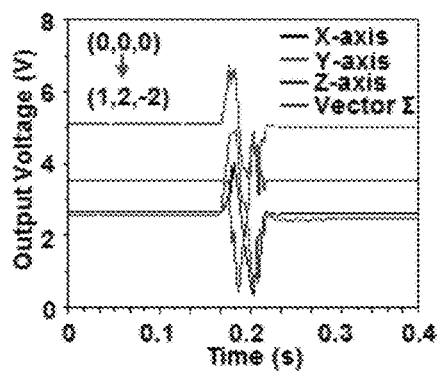
[FIG. 20B]
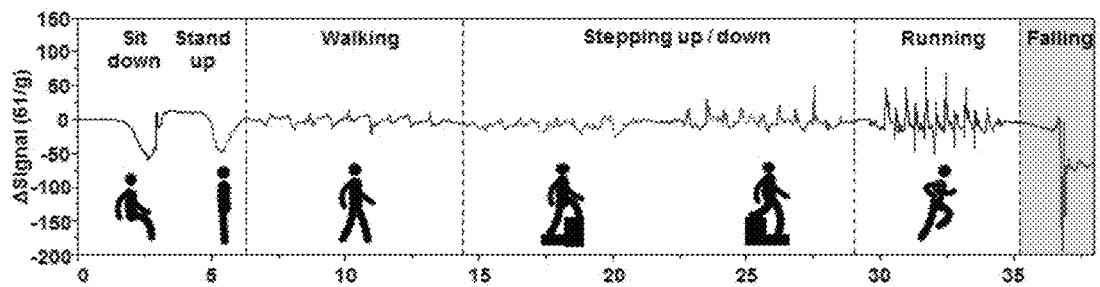
[FIG. 20C]
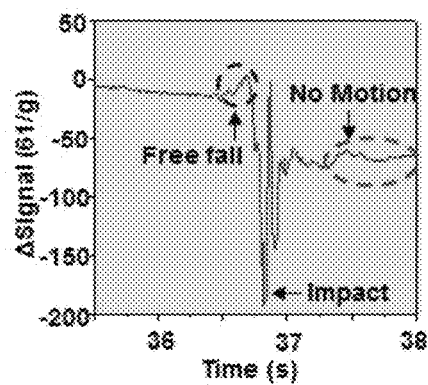

[FIG. 20D]
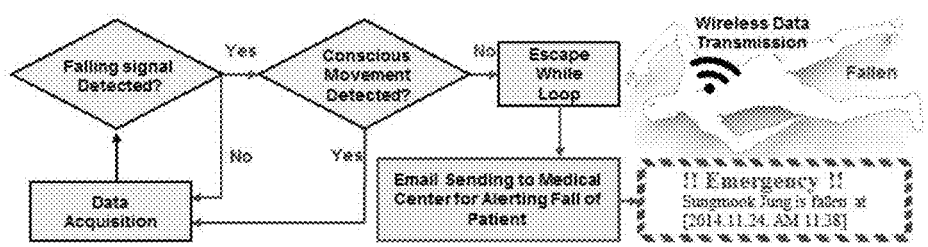
[FIG. 21]
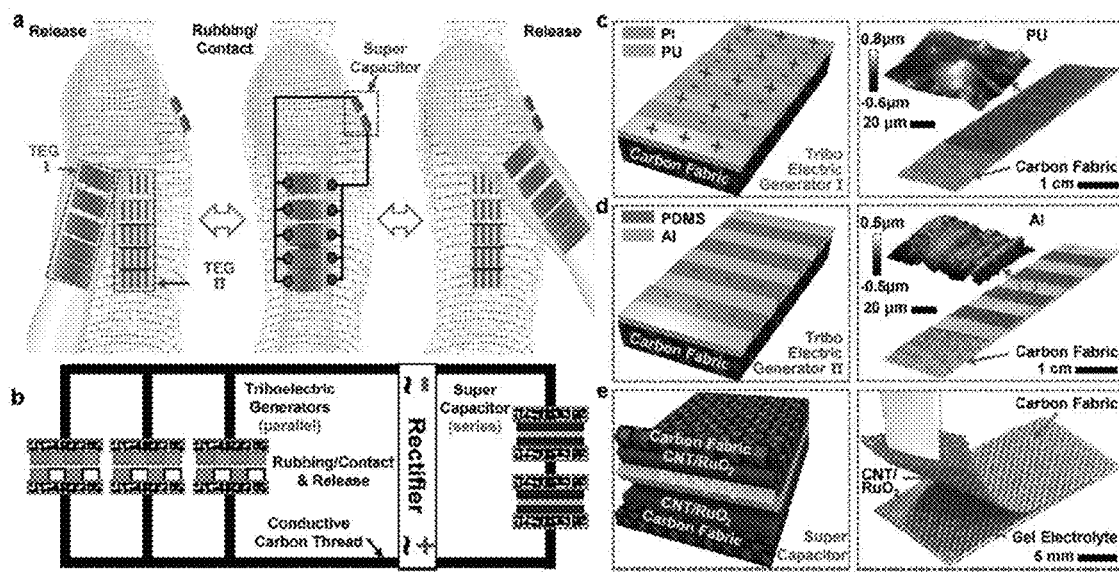

[FIG. 22]
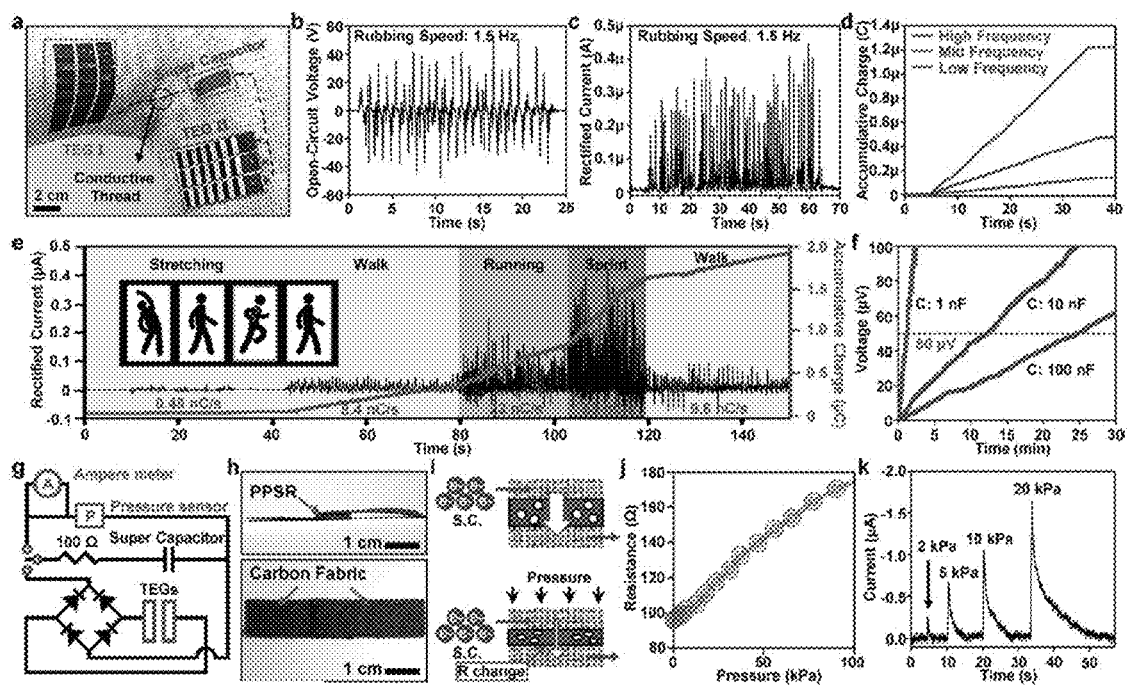

STRETCHABLE TRIBOELECTRIC GENERATOR, STRETCHABLE ELECTRICITY STORAGE DEVICE, AND WEARABLE ELECTRONIC DEVICE

BACKGROUND

1. Technical Field

The present disclosure relates to a stretchable triboelectric generator, a stretchable electricity storage device and a wearable electronic device.

2. Description of the Related Art

Recently wearable electronics have attracted great attention for various reasons such as convenience. However, all energy related components, for example, triboelectric generators and batteries, were not yet seamlessly integrated with sensors, wireless communication units, and controller in one wearable platform.

In order to easily apply energy related components to the wearable electronic device, stretchability is needed for the components.

SUMMARY

Accordingly, the present disclosure has been made keeping in mind the above problems occurring in the related art, and an object of the present disclosure is to provide a stretchable triboelectric generator.

Another object of the present disclosure is to provide a stretchable electricity storage device.

Still another object of the present disclosure is to provide a wearable electronic device comprising the stretchable triboelectric generator and/or the stretchable electricity storage device.

Other objects of the present disclosure will be apparent to those skilled in the art from the reading of the following description with reference to the accompanying drawings.

In order to achieve the above object, the present disclosure provides a stretchable triboelectric, comprising a first stretchable triboelectric generation part comprising a first fabric layer and a first friction layer on the first fabric layer and a second stretchable triboelectric generation part comprising a second fabric layer and a second friction layer on the second fabric layer.

A work function of the first friction layer may be different from a work function of the second friction layer.

A charge amount by triboelectrification of the first friction layer and the second friction layer may be determined by a difference between the work function of the first friction layer and that of the second friction layer.

The first friction layer may comprise PEIE and the second friction layer may comprise silicone rubber.

The first friction layer may comprise first friction patterns and second friction patterns disposed alternatingly, and the second friction layer may comprise third friction patterns and fourth friction patterns disposed alternatingly.

The first friction patterns, the second friction patterns, the third friction patterns, and the fourth friction patterns each may have a different surface roughness.

The first friction patterns may comprise polyurethane, the second friction patterns may comprise polyimide, the third friction patterns may comprise polydimethylsiloxane, and the fourth friction patterns may comprise aluminum (Al).

The first friction patterns and the second friction patterns may have substantially the same thickness, and the third friction patterns and the fourth friction patterns may have substantially the same thickness.

The first fabric layer and the second fabric layer may comprise at least one of conductive nylon fabric or conductive carbon fabric.

The stretchable triboelectric generator according to embodiments of the present disclosure may be easily attached to or sewn into fabric such as clothes and be formed to have a wristband shape because of having stretchability. The stretchable triboelectric generator may have good friction electricity characteristics and generate electricity by horizontal friction and vertical friction. The stretchable friction generator may generate friction electricity through daily activities and be easily applied to a wearable electronic device.

The present disclosure provides a stretchable electricity storage device, comprising at least one of a stretchable battery or a stretchable supercapacitor. The stretchable electricity storage device may be connected to the stretchable triboelectric generator and may store electricity generated by the stretchable triboelectric generator.

The stretchable battery may comprise a third fabric layer, a cathode electrode on the third fabric layer, a separator on the cathode electrode, an electrolyte layer on the separator, an anode electrode on the electrolyte layer, and a fourth fabric layer on the anode electrode.

At least one of the separator, the third fabric layer, or the fourth fabric layer may have a repeatedly bent shape or an at least partially bent shape.

The separator may comprise at least one of polypropylene film or polyethylene film.

The third fabric layer and the fourth fabric layer may comprise at least one of conductive nylon fabric or conductive carbon fabric.

The supercapacitor may comprise a third fabric layer, a first catalyst layer on the third fabric layer, a first electrode layer on the first catalyst layer, a electrolyte layer on the first electrode layer, a second electrode layer on the electrolyte layer, a second catalyst layer on the second electrode layer, and a fourth fabric layer on the second catalyst layer.

The first electrode layer and the second electrode layer may comprise carbon nanotubes grown substantially vertically to the third fabric layer and the fourth fabric layer, and the carbon nanotubes may comprise $RuO_2$ nanoparticles or $RuO_2$ layer formed on the surface of the carbon nanotubes.

The first catalyst layer and the second catalyst layer may comprise Al layer and Fe layer.

The third fabric layer and the fourth fabric layer may comprise at least one of conductive nylon fabric or conductive carbon fabric.

The stretchable electricity storage device according to embodiments of the present disclosure may be easily attached to or sewn into fabric such as clothes and be formed to have a wristband shape because of having stretchability. The stretchable electricity storage device may have good electricity (power, energy) storage characteristics. The stretchable electricity storage device may be easily applied to a wearable electronic device.

The present disclosure provides a wearable electronic device, comprising the stretchable triboelectric generator, the stretchable electricity storage device and a sensor connected electrically to at least one of the stretchable triboelectric generator or the stretchable electricity storage device to sense vital signs, bio signals, or body's movement changes.

The sensor may be a 3-axis accelerometer.

The wearable electronic device according to embodiments of the present disclosure may comprise the stretchable triboelectric generator and the stretchable electricity storage device, and generate, store and use electricity continuously. The wearable electronic device may harvest, store and use electricity generated through daily activities, and realize various wearable devices such as fall detection device, medical device.

BRIEF DESCRIPTION OF THE DRAWINGS

The above and other objects, features and advantages of the present disclosure will be more clearly understood from the following detailed description taken in conjunction with the accompanying drawings, in which:

FIG. 1 is a sectional view showing a triboelectric generator according to an embodiment of the present disclosure;

FIGS. 2A and 2B illustrate a method for forming the triboelectric generator of FIG. 1;

FIG. 3 illustrates chemical structure of surface of a triboelectric generator according to an embodiment of the present disclosure;

FIG. 4 illustrates energy-level diagrams of a triboelectric generator according to an embodiment of the present disclosure;

FIGS. 5A and 5B illustrate comparative SEM images of a PEIE-coated conductive nylon layer according to an embodiment of the present disclosure and a bare conductive nylon layer;

FIGS. 6A to 6E illustrate current and voltage characteristics of a PEIE-coated conductive nylon layer according to an embodiment of the present disclosure;

FIG. 7 illustrates electricity generated from living activities by a triboelectric generator according to an embodiment of the present disclosure;

FIG. 8 is a sectional view of a triboelectric generator according to another embodiment of the present disclosure;

FIGS. 9A to 9F illustrate a method for forming the triboelectric generator of FIG. 8;

FIG. 10 illustrates a structure and mechanism of a triboelectric generator according to another embodiment of the present disclosure;

FIG. 11 illustrates short-circuit current generated by continuous rubbing or discrete rubbing of a triboelectric generator according to another embodiment of the present disclosure;

FIG. 12 is a sectional view of a battery according to yet another embodiment of the present disclosure;

FIGS. 13A to 13C illustrate a method for forming the battery of FIG. 12;

FIG. 14 is a sectional view of a battery according to yet another embodiment of the present disclosure;

FIG. 15 is a sectional view of a battery according to yet another embodiment of the present disclosure;

FIG. 16 is a sectional view of a supercapacitor according to yet another embodiment of the present disclosure;

FIGS. 17A to 17C illustrate a method for forming the supercapacitor of FIG. 16;

FIG. 18 illustrates a structure and electrochemical characteristics of a supercapacitor according to yet another embodiment of the present disclosure;

FIGS. 19A to 19E illustrate a wearable electronic device according to yet another embodiment of the present disclosure;

FIGS. 20A to 20D illustrate application examples of the wearable electronic device of FIG. 19A;

FIG. 21 illustrates a structure and motion principle of a wearable electronic device according to yet another embodiment of the present disclosure; and FIG. 22 illustrates demonstration and measurement of electrical signals of the wearable electronic device of FIG. 21.

DESCRIPTION OF PREFERRED EMBODIMENTS

Hereinafter, the present disclosure will be described in detail with reference to embodiments. The above and other objects, features, and advantages of the present disclosure will be apparent from a reading of the following embodiments. The present disclosure is not limited to embodiments described herein, but may be embodied in various forms. While preferred embodiments are described herein, it is to be understood that they merely make the disclosure more thorough and complete and aid in completely understanding those skilled in the art. Therefore, the disclosure should not be limited to the following embodiments.

For clarity and convenience of description, the size of components shown in the drawings may not be illustrated to scale. Further, the shape of components shown in the drawings may be somewhat changed if necessary. Therefore, it should be understood that the disclosure is not limited to the embodiments taken in conjunction with the accompanying drawings unless otherwise specifically stated, and that changes and variations may be made without departing from the spirit or scope of the claims.

It should be understood that when an element or layer (or film) is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present.

It should be understood that, although the terms first, second, etc. are used herein to describe various elements, these elements should not be limited by these terms. These terms are only used to distinguish one element from another. For example, a first element could be termed a second element, and similarly, a second element could be termed a first element, without departing from the scope of example embodiments. As used herein, the term "and/or" includes any and all combinations of one or more of the associated listed items.

The terminology used herein is for the purpose of describing example embodiments only and is not intended to be limiting of the example embodiments. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Terms, "stretchable" and "stretchability", used herein have the meaning including "flexible" and "flexibility".

Example embodiments described below with respect to the drawings are provided so that this disclosure will be thorough, complete and fully convey the concept of example embodiments to those skilled in the art. In the drawings, like numbers refer to like elements throughout. Further, the thicknesses of layers and regions are exaggerated for clarity in the drawings.

Stretchable Triboelectric Generator

FIG. 1 is a sectional view showing a triboelectric generator according to an embodiment of the present disclosure.

Referring to FIG. 1, a triboelectric generator 100 comprises a first triboelectric generator 110 and a second triboelectric generator 120. The first triboelectric generator 110 may comprise a first fabric layer 111 and a first friction layer 112 and a second triboelectric generator 120 may comprise a second fabric layer 121 and a second friction layer 122.

The first fabric layer 111 and the second fabric layer 121 may include conductive nylon fabric, conductive carbon fabric and so on and have stretchability.

The first friction layer 112 may be provided on the surface of the first fabric layer 111. The first friction layer 112 may be a coating layer coating the surface of the first fabric layer 111 or a surface modified layer modifying the surface of the first fabric layer 111.

The second friction layer 122 may be provided on the surface of the second fabric layer 121. The second friction layer 122 may be a coating layer coating the surface of the second fabric layer 121 or a surface modified layer modifying the surface of the second fabric layer 121.

The first friction layer 112 and the second friction layer 122 may include materials having different work function to each other. The work function of the first friction layer 112 may be different from that of the second friction layer 122. Preferably, the first friction layer 112 and the second friction layer 122 may include materials of which work function gap is large. That is, the work function gap between the first friction layer 112 and the second friction layer 122 may be large. For example, the first friction layer 112 may include PEIE (polyethyleneimine ethoxylated) and the second friction layer 122 may include silicone rubber. The PEIE has a relatively low work function of 6.99 eV and the silicone rubber has a relatively high work function of 14.15 eV. The silicone rubber may increase the stretchability of the triboelectric generator 100 because the silicone rubber has a low Young's modulus.

The first friction layer 112 and the second friction layer 122 may be disposed to face each other and the triboelectric generator 100 may generate frictional electricity by contact/release friction between the first friction layer 112 and the second friction layer 122. The charge amount due to triboelectrification of the first friction layer 112 and the second friction layer 122 may be determined by the work function gap between the first friction layer 112 and the second friction layer 122. The frictional electricity may be enhanced as the work function gap is larger. The first triboelectric generation part 110 and the second triboelectric generation part 120 may be tailored and equipped on clothes by weaving or may be bent and then both the ends may be pasted up with each other to form the wrist band shape. For example, the first triboelectric generation part 110 may be tailored and equipped on clothes by weaving and the second triboelectric generation part 120 may be bent and then both the ends of the second triboelectric generation part may be pasted up with each other to form the wristband shape.

FIGS. 2A and 2B illustrate a method for forming the triboelectric generator of FIG. 1.

Referring to FIG. 2A, the first friction layer 112 is formed on the surface of the first fabric layer 111. The first fabric layer 111 may be formed with conductive nylon fabric, conductive carbon fabric and so on. The first friction layer 112 may be formed with PEIE. For example, the first friction layer 112 may be formed by coating the surface of the first fabric layer 111 with PEIE solution diluted with anhydrous ethanol and drying the PEIE solution.

Referring to FIG. 2B, the second friction layer 122 is formed on the surface of the second fabric layer 121. The second fabric layer 121 may be formed with conductive nylon fabric, conductive carbon fabric and so on. The second friction layer 122 may be formed with silicone rubber. For example, the second friction layer 122 may be formed by coating the surface of the second fabric layer 121 with the silicone rubber and curing the silicone rubber.

Thereby the triboelectric generator 100 comprising the first triboelectric generation part 110 and the second triboelectric generation part 120 may be formed.

FIG. 3 illustrates chemical structure of surface of a triboelectric generator according to an embodiment of the present disclosure, and FIG. 4 illustrates energy-level diagrams of a triboelectric generator according to an embodiment of the present disclosure.

Referring to FIGS. 3 and 4, the charge amount due to triboelectrification of the triboelectric generator may be determined by the work function gap between the first triboelectric generation part (C-Nylone/PEIE) and the second triboelectric generation part (C-Nylon/Silicone rubber). The surfaces of conductive nylon layers (C-Nylon) may be coated or modified with materials having different work function, for example, PEIE and silicone rubber for high friction electricity effect. The surface of the conductive nylon layer (C-Nylon) of the first triboelectric generation part (C-Nylon/PEIE) may be coated or modified with PEIE having relatively low work function (6.99 eV), and the surface of the conductive nylon layer (C-Nylon) of the second triboelectric generation part (C-Nylon/Silicone rubber) may be coated or modified with silicone rubber having relatively high work function (14.15 eV). The silicone rubber may increase stretchability of the triboelectric generator because of having a low Young's modulus. Friction electricity effect may be enhanced as the surfaces of the conductive nylon layers (C-Nylon) of the first triboelectric generation part (C-Nylon/PEIE) and the second triboelectric generation part (C-Nylon/Silicone rubber) are coated or modified with PEIE and silicone rubber of which the work function gap is large.

FIGS. 5A and 5B illustrate comparative SEM images of a PEIE-coated conductive nylon layer according to an embodiment of the present disclosure and a bare conductive nylon layer.

Referring to FIGS. 5A and 5B, it is confirmed that the surface of the conductive nylon layer (C-Nylon) is modified with PEIE. The surface of the bare (uncoated) conductive nylon layer (Bare C-Nylon) may have hydrophobicity that beads of water form on the surface of the bare conductive nylon layer (Bare C-Nylon) and so on, but the surface of the conductive nylon layer (C-Nylon/PEIE) modified with PEIE may have hydrophilicity that beads of water do not formed on the surface of the surface and so on. The PEIE surface modified conductive nylon layer (C-Nylon/PEIE) may be stretchable to 125% without damage.

FIGS. 6A to 6E illustrate current and voltage characteristics of a PEIE-coated conductive nylon layer according to an embodiment of the present disclosure.

Referring to FIG. 6A, the triboelectric voltage of the PEIE surface modified conductive nylon layer (C-Nylon/PEIE) increases up to 3 times compared to that of the bare conductive nylon layer (C-Nylon), while the mechanical property (stiffness) of the PEIE surface modified conductive nylon layer is barely changed and remains soft, according to the triboelectricity measured by Korean standard triboelectric voltage measurement.

Referring to FIGS. 6B and 6C, the triboelectric voltage of the PEIE surface modified conductive nylon layer (C-Nylon/PEIE) increases up from 29V to 66V compared to the bare conductive nylon layer (C-Nylon) and the triboelectric current increases up from 78 nA to 159 nA.

Referring to FIG. 6D, as the contact pressure increases, the performance of the triboelectric generator proportionally increases from 36 V (0.3 kPa) to 104 V (6.7 kPa).

Referring to FIG. 6E, the thickness of the silicone rubber and the load resistance are 2 mm and 400 MΩ where optimum performances are shown at the fixed contact pressure and frequency of 1.1 kPa and 0.7 Hz which are analogous to contact conditions between the sleeve and the wrist during normal daily activities.

FIG. 7 illustrates electricity generated from living activities by a triboelectric generator according to an embodiment of the present disclosure.

Referring to FIG. 7, the triboelectric generator generates the electricity through motions such as walking and running and running makes higher and more frequent current peaks than walking.

Example 1 For Manufacturing a Stretchable Triboelectric Generator

A conductive nylon layer was coated with PEIE solution (80% ethoxylated solution) diluted in anhydrous ethanol with concentration of 4~20 wt %. The PEIE solution was spread on the conductive nylon layer and blown by N2 gas, and then dried in a convection oven at 55° C. for 6 hr. The repetition of the above process was made up to 6 times. The PEIE coated fabric was tailored and equipped on clothes by weaving. Thereby a first triboelectric generation part was formed.

A conductive nylon layer was coated with silicone rubber. The silicone rubber was cured in the convection oven over about 4 hours at about 70° C. Thereby a second triboelectric generation part was formed. The second triboelectric generation part was bent and then both the ends of the second triboelectric generation part were pasted up with each other to form the wristband shape.

As stated above, a triboelectric generator was formed by the first triboelectric generation part and the second triboelectric generation part.

FIG. 8 is a sectional view of a triboelectric generator according to another embodiment of the present disclosure.

Referring to FIG. 8, a triboelectric generator 100 comprises a first triboelectric generation part 110 and a second triboelectric generation part 120. The first triboelectric generation part 110 may comprise a first fabric layer 111 and a first friction layer 112 and the second triboelectric generation part 120 may comprise a second fabric layer 121 and a second friction layer 122.

The first fabric layer 111 and the second fabric layer 121 may include conductive nylon fabric, conductive carbon fabric and so on and have stretchability.

The first friction layer 112 may be provided on the surface of the first fabric layer 111. The first friction layer 112 may comprise first friction patterns 112a and second friction patterns 112b which are disposed alternatingly to each other. The first friction patterns 112a and the second friction patterns 112b may have substantially the same thickness.

The second friction layer 122 may be provided on the surface of the second fabric layer 121. The second friction layer 122 may comprise third friction patterns 122a and fourth friction patterns 122b. The third friction patterns 122a and the fourth friction patterns 122b may have substantially the same thickness.

The first friction layer 112 and the second friction layer 122 may be disposed to face each other and the triboelectric generator 100 may generate frictional electricity by contact/release friction between the first friction layer 112 and the second friction layer 122. The triboelectric generator can generate frictional electricity through both horizontal and vertical friction of the first friction layer 112 and the second friction layer 122.

The first friction patterns 112a, the second friction patterns 112b, the third friction patterns 122a, and the fourth friction patterns 122b may be include materials having different surface roughnesses to each other. For example, the first friction patterns 112a may include polyurethane (PU) or polyurethane acrylate (PUA) and the second friction patterns 112b may include polyimide (PI). The third friction patterns 122a may include polydimethylsiloxane (PDMS) and the fourth friction patterns 122b may include aluminum (Al). The quadratic mean roughness (Rq) of the polyurethane is 158 nm and the quadratic mean roughness (Rq) of the polyimide (PI) is 23.5 nm. The quadratic roughness (Rq) of the polydimethylsiloxane (PDMS) is 49.4 nm and the quadratic mean roughness (Rq) of the aluminum (Al) is 200 nm.

The first triboelectric generation part 110 and the second triboelectric generation part 120 may be tailored and equipped on clothes by weaving. The first triboelectric generation part 110 and the second triboelectric generation part 120 may be disposed in an armpit region to maximize friction FIGS. 9A to 9D illustrate a method for forming the triboelectric generator of FIG. 8.

Referring to FIG. 9A, first sacrifice patterns 112p are formed at regular intervals on the first fabric layer 111. The first fabric layer 111 may be formed with conductive nylon fabric, conductive carbon fabric and so on and the first sacrifice patterns 112p may be formed with polyimide.

Referring to FIG. 9B, the first friction patterns 112a are formed between the first sacrifice patterns 112p and then the first sacrifice patterns 112p are removed. The first friction patterns 112a may be formed with polyurethane or polyurethane acrylate.

Referring to FIG. 9C, the second friction patterns 112b are formed between the first friction patterns 112a. The second friction patterns 112b may be formed with polyimide. The first friction patterns 112a and the second friction patterns 112b may be formed to have substantially the same thickness.

Referring to FIG. 9D, second sacrifice patterns 122p are formed at regular intervals on the second fabric layer 121. The second fabric layer 121 may be formed with conductive nylon fabric, conductive carbon fabric and so on and the second sacrifice patterns 112p may be formed with polyimide.

Referring to FIG. 9E, the third friction patterns 122a are formed between the second sacrifice patterns 122p and then the second sacrifice patterns 122p are removed. The third friction patterns 122a may be formed with polydimethylsiloxane.

Referring to FIG. 9F, the fourth friction patterns 122b are formed between the third friction patterns 122a. The fourth friction patterns 122b may be formed with aluminum. The third friction patterns 122a and the fourth friction patterns 122b may be formed to have substantially the same thickness.

FIG. 10 illustrates a structure and mechanism of a triboelectric generator according to another embodiment of the present disclosure.

Referring to FIGS. 10a to 10d, the polarity of the induced current is determined by the relative position of friction patterns. For example, positive and negative peaks are observed as aluminum (Al) is aligned with polyurethane (PU) and polyimide (PI) respectively. Given that the aluminum conducting layer transmits electrons to the electrode, it plays a role as a charge reservoir. The electrical current output is monitored by connecting the first triboelectric generation part (TEG I) and the second triboelectric generation part (TEG II) to the ground and signal lines respectively. As shown in FIG. 10B, when aluminum (Al) is dragged toward polyurethane (PU), it tends to neutralize the positively charged polyurethane (PU) surface by supplying electrons. This is shown as the upper peaks in FIG. 10c. When aluminum (Al) is dragged toward polyimide (PI), it withdraws electrons from the negatively charged polyimide (PI) surface. This is shown as the bottom peaks in FIG. 10c. Positively charged polyurethane (PU) and negatively charged polyimide (PI) surfaces are formed through their frictional contact with polydimethylsiloxane (PDMS), and due to the triboelectric series, polydimethylsiloxane (PDMS) and polyurethane (PU) become fully saturated with electrons and holes respectively. As electron-saturated polydimethylsiloxane (PDMS) slides toward polyimide (PI), electrons move from polydimethylsiloxane (PDMS) to polyimide (PI) and polydimethylsiloxane (PDMS) and polyimide (PI) share electrons. As shown in FIG. 10d, the amount of charge transferred remains much the same regardless of flow direction.

FIG. 10e illustrates a schematic diagram of the principles by which the triboelectric generator converts vertical friction in the contact/release mode to electrical energy.

Referring to FIGS. 10f and 10g, To characterize the performance of the triboelectric generator (TEG), Isc (short-circuit current) and Voc (open-circuit voltage) were measured at the moderate rubbing speed of 3 cm/s, which is analogous to the swing speed of the human arm at normal walking pace, using a friction distance of 5 mm. Isc exhibits a proportional relationship (6 line: 23 nA, 12 line: 43 nA, 18 line: 55 nA) to the number of repeated friction patterns (Length: 1.5 cm, Width: 0.5 cm, Area: 0.75 cm$^2$ for each pattern). Furthermore, although Voc increases up to 6 V, it becomes stagnant as the area increases beyond 12 lines due to the input impedance of the measurement system.

Referring to FIGS. 10h and 10i, when subjected to contact/release friction, triboelectric generators with the same surface area generates an electrical current of about 130 nA and a voltage of about 15 V.

Referring to FIGS. 10j to 10m, the AC output is converted to DC via a rectifying diode. FIGS. 10j and 10k show the accumulated current during rubbing and contact/release. Although the peak value (FIG. 10l) of Isc induced by rubbing is not as regular as the peak value (FIG. 10m) of contact/release friction, the accumulated current exhibits a linear increase under both rubbing friction and contact/release friction due to the similarity of the integrated area of each peak.

FIG. 11 illustrates short-circuit current generated by continuous rubbing or discrete rubbing of a triboelectric generator according to another embodiment of the present disclosure. Top row figures of FIG. 11 show the continuous rubbing and mid row figures show the discrete rubbing. FIG. 11a shows the case that the thickness of aluminum (Al) pattern is 0.4 mm, FIG. 11b shows the case that the thickness of aluminum (Al) pattern is 0.1 mm, and FIG. 11c shows the case that the thickness of aluminum (Al) pattern is 0.2 mm. The thicknesses of all other polymer patterns (polydimethylsiloxane (PDMS) pattern, polyurethane (PU) pattern, and polyimide (PI) pattern) is fixed at 0.2 mm. The first triboelectric generation part disposed above the second triboelectric generation part comprises polyurethane (PU) pattern and polyimide (PI) pattern and the second generation part disposed under the first triboelectric generation part comprises polydimethylsiloxane (PDMS) pattern and aluminum (Al) pattern.

Referring to FIG. 11a, during rubbing, only aluminum (Al) pattern makes contact with the polymer patterns (polyurethane (PU) pattern and polyimide (PI) pattern) of the first triboelectric generation part (TEG I) and aluminum (Al) pattern tends to deliver or withdraw electrons onto polyimide (PI) pattern and polyurethane (PU) pattern respectively. The PDMS covered area of the carbon fabric drives electrons back and forth by electrostatic induction along with the electrification of aluminum pattern. Unusual current outputs with both positive and negative peaks are frequently observed, which can be explained by free electrons in aluminum (Al) pattern. When aluminum (Al) pattern induces a triboelectric charge in the polymer patterns in the first triboelectric generation part (TEG I), it may give or take back electrons.

Referring to FIG. 11b, only polydimethylsiloxane (PDMS) pattern makes contact with the polymer patterns (polyurethane (PU) pattern and polyimide (PI) pattern) of the first triboelectric generation part (TEG I) and the polarity of the current output is inversed. This can be explained by the sum of two kinds of current induction of electrostatic induction and dynamic electrification. The electrostatic induction is induced by contact/release behaviors of polydimethylsiloxane (PDMS) pattern during rubbing. When the negatively charged polydimethylsiloxane (PDMS) pattern is dragged from polyurethane (PU) pattern to polyimide (PI) pattern, polyurethane (PU) pattern exposed to the air loses the negative circumstances (release) while polyimide (PI) pattern gains the negative circumstances (contact). Due to the contact/release induced by same polydimethylsiloxane (PDMS), the amount of induced current is equal and the direction of induced currents are contrary to each other which made the total zero output current. The dynamic electrification is induced by friction between polydimethylsiloxane (PDMS) pattern and the polymer patterns of the first triboelectric generation part (TEG I). Polydimethylsiloxane (PDMS) pattern electrified by polyurethane (PU) pattern causes electrons to flow back in the bottom fabric while polyimide (PI) pattern causes electrons to flow forward in the upper fabric.

Referring to FIG. 11c, when both polydimethylsiloxane (PDMS) pattern and aluminum (Al) pattern make contact with polymer patterns of the first triboelectric generation part (TEG I), the current peaks show an identical flow regardless of the direction.

Example 2 For Manufacturing a Stretchable
Triboelectric Generator 5 mm wide polyimide (PI) tapes were disposed at 5 mm intervals on conductive carbon fabric. Polyurethane acrylate (PUA) was poured over the conductive carbon fabric and PET film was placed over the top and pressed to form uniform thickness of the PUA film. After solidifying the PUA by irradiating it for 12 hr under an ultraviolet (UV) lamp, the PI tapes were removed. PI tapes were stacked on the exposed area of the conductive carbon fabric until the surface was made level. Thereby a first triboelectric generation part was formed.

5 mm wide aluminum (Al) tapes were disposed at 5 mm intervals on conductive carbon fabric. The Al tapes were covered by PI tapes and polydimethylsiloxane (PDMS) (10:1 mixture of prepolymer:curing agent) was poured over the conductive carbon fabric. A PI covered PET film was placed over the PDMS and pressed by a 3 kg stainless steel plate to form a uniform thickness of PDMS film. After curing the PDMS in a convection oven at 90° C. for more than 12 hr, the PI tapes were removed. Additional Al tapes were stacked on the Al tapes until the surface was made level. Thereby a second triboelectric generation part was formed.

The first triboelectric generation part and the second triboelectric generation part were attached to a fabric by a fabric bonding agent and sewn by a conductive thread and then a stretchable triboelectric generator was formed.

[Stretchable Electricity Storage Device]
<Stretchable Battery>

FIG. 12 is a sectional view of a battery according to yet another embodiment of the present disclosure.

Referring to FIG. 12, a battery 200 may comprise a first fabric layer 211, a cathode electrode 221, a separator 230, an electrolyte layer 240, an anode electrode 222, and a second fabric layer 212.

The first fabric layer 211 and the second fabric layer 212 may include conductive nylon fabric, conductive carbon fabric and so on and have stretchablility. The first fabric layer 211 and the second fabric layer 212 may function as a current collector.

The cathode electrode 221 may include active material for cathode. The active material for cathode may include, for example, $LiCoO_2$ (Lithium cobalt oxide, LCO). The cathode electrode 221 may further include carbon black and PVDF (Polyvinylidene difluoride) binder dissolved in NMP (N-methyl-2-pyrrolidone).

The anode electrode 222 may include active material for anode. The active material for anode may include, for example, $Li_4Ti_5O_{12}$ (Lithium titanate, LTO). The anode electrode 222 may further include carbon black and PVDF (Polyvinylidene difluoride) binder dissolved in NMP (N-methyl-2-pyrrolidone).

The separator 230 may include at least one of polypropylene film or polyethylene film. For example, the separator 230 may be a single film of the polypropylene film or the polyethylene film or may be a stacked film of the polypropylene film and/or the polyethylene film. The separator 230 may have repeatedly bent shape and thereby the stretchability of the separator 230 may be enhanced. Unlike this embodiment, the separator 230 may have at least partially bent shape.

The electrolyte layer 240 may be a gel type film. The electrolyte layer 240 may be formed to be the gel type film by dissolving polymer such as polyethylene oxide in EC (Ethylene carbonate)/DMC (Dimethyl carbonate) solution in which $LiClO_4$ is dissolved.

The first fabric layer 211 and the second fabric layer 222 may comprise a coating layer (not shown in FIG. 12) on the contact surface with the cathode electrode and the anode electrode. The coating layer may be formed by coating the surfaces of the first fabric layer 211 and the second fabric layer 222 with Ni using electroless plating method.

An encapsulation layer (not shown in FIG. 12) may further disposed above and/or under battery 200. The encapsulation layer may play a role in supporting and protecting the battery 200. For example, the encapsulation layer may be formed with silicone rubber.

FIGS. 13A to 13C illustrate a method for forming the battery of FIG. 12.

Referring to FIG. 13A, the cathode electrode 221 is formed on the first fabric layer 211. The first fabric layer 211 may be formed with conductive nylon fabric, conductive carbon fabric and so on.

The cathode electrode 221 may be formed by applying a mixture of active material for cathode, carbon black, and PVDF binder dissolved in NMP on the first fabric layer 211 and drying the applied mixture under vacuum. For example, the active material for cathode may include $LiCoO_2$, and the active material for cathode, the carbon black, and the PVDF binder dissolved in NMP may be mixed at the weight ratio of 8:1:1 in the mixture.

A coating layer (not shown in FIG. 13A) may be further formed on the first fabric layer 211 before forming the cathode electrode 221. The coating layer may be formed by coating the surface of the first fabric layer 211 with Ni using electroless plating method. For example, the coating layer may be formed by dipping the first fabric layer 211 in the aqueous solution of $NiSO_4$ (Nickel(II) sulfate), $Na_4P_2O_7$ (Sodium pyrophosphate tetrabasic), and $NH(CH_3)_2BH_3$ (Borane dimethylamine complex) for predetermined time and cleaning it with DI water and ethanol.

Referring to FIG. 13B, the anode electrode 222 is formed on the second fabric layer 212. The second fabric layer 212 may be formed with conductive nylon fabric, conductive carbon fabric and so on.

The anode electrode 222 may be formed by applying a mixture of active material for anode, carbon black, and PVDF binder dissolved in NMP on second fabric layer 212 and drying the applied mixture under vacuum. For example, the active material for anode may include $Li_4Ti_5O_{12}$, and the active material for anode, the carbon black, and the PVDF binder dissolved in NMP may be mixed at the weight ratio of 8:1:1 in the mixture.

A coating layer (not shown in FIG. 13B) may be further formed on the second fabric layer 212 before forming the anode electrode 222. The coating layer may be formed by coating the surface of the second fabric layer 212 with Ni using electroless plating method. For example, the coating layer may be formed by dipping the second fabric layer 212 in the aqueous solution of $NiSO_4$, $Na_4P_2O_7$, and $NH(CH_3)_2BH_3$ for predetermined time and cleaning it with DI water and ethanol.

Referring to FIC. 13C, the separator 230 and the electrolyte layer 240 are provided between the cathode electrode 231 and the anode electrode 232.

The separator 230 may be formed with at least one of polypropylene film or polyethylene film. For example, the separator 230 may be formed to be a single film of the polypropylene film or the polyethylene film or to be a stacked film of the polypropylene film and/or the polyethylene film. The separator 230 may have repeatedly bent shape.

The electrolyte layer 240 may be formed to be the gel type film by dissolving polymer such as polyethylene oxide in EC (Ethylene carbonate)/DMC (Dimethyl carbonate) solution in which $LiClO_4$ is dissolved.

FIG. 14 is a sectional view of a battery according to yet another embodiment of the present disclosure.

Referring to FIG. 14, the first fabric layer 211 with the cathode electrode 221 and the second fabric layer 212 with the anode electrode 222 may have repeatedly bent shape. A silicone rubber layer is expanded and the surface (opposite to the surface contacting with the cathode electrode 221) of the first fabric layer is bonded at regular intervals to the expanded silicone rubber layer. Then the silicone rubber layer returns to original state before expanding and the parts of the first fabric layer which are not bonded to the expanded silicone rubber layer are bent. Thereby the first fabric layer 211 having repeatedly bent shape may be formed. Like this, second fabric layer 212 having repeatedly bent shape may be formed. Unlike this embodiment, only one of the first fabric layer 211 and the second fabric layer 212 may have repeatedly bent shape.

FIG. 15 is a sectional view of a battery according to yet another embodiment of the present disclosure.

Referring to FIG. 15, the separator 230 may have flat shape in the region between the cathode electrode 221 and the anode electrode 222 and bent shape in the region of both end parts. The stretchability of the battery 200 may be enhanced by the bent shape. Unlike this embodiment, the separator 230 may have bent shape only in the region of one end part or only in the region between the cathode electrode 221 and the anode electrode 222.

Example for Manufacturing a Stretchable Battery

A conductive nylon layer was coated with NI by electroless plating method. The conductive nylon layer coated with Ni can function as a current collector. The conductive nylon layer was dipped in the aqueous solution of 260 mM $NiSO_4$, 75 mM $Na_4P_2O_7$, and 34 mM $NH(CH_3)_2BH_3$ for about one (1) hour and cleaned with DI water and ethanol. The conductive nylon layer coated with Ni was dipped for 1 min in gold etchant to remove exposed Ag of the conductive nylon layer and then cleaned with DI water and ethanol continuously.

An electrode for lithium ion battery was formed by a mixture in which active material, carbon black, and PVDF binder dissolved in NMP were mixed at the weight ratio of 8:1:1. $LiCoO_2$ (LCO) may be used as active material for cathode and $Li_4Ti_5O_{12}$ (LTO) may be used as active material for anode. Cathode electrode was formed by coating Ni coated conductive nylon layer with the mixture including the LCO as the active material and drying it under vacuum at 80° C. for 12 hr. Anode electrode was formed by coating Ni coated conductive nylon layer with the mixture including the LTO as the active material and drying it under vacuum at 80° C. for 12 hr.

A stretchable lithium ion battery was formed by disposing a polypropylene separator and an electrolyte layer between the cathode electrode and the anode electrode. The polypropylene separator may have repeatedly bent shape or at least partially bent shape. The electrolyte layer may be formed by applying EC/DMC (v/v=1/1) solution in which 1M $LiClO_4$ is dissolved.

<Stretchable Supercapacitor>

FIG. 16 is a sectional view of a supercapacitor according to yet another embodiment of the present disclosure.

Referring to FIG. 16, a supercapacitor 300 may comprise a first fabric layer 311, a first catalyst layer 321, a first electrode layer 331, an electrolyte layer 340, a second electrode layer 332, a second catalyst layer 322, and a second fabric layer 312.

The first fabric layer 311 and the second fabric layer 312 may include conductive nylon fabric, conductive carbon fabric and so on and have stretchability.

The first catalyst layer 321 and the second catalyst layer 322 may include an aluminum (Al) layer and an iron (Fe) layer. The aluminum layer and the iron layer may be formed by thermal deposition and e-beam deposition.

The first electrode layer 331 and the second electrode layer 332 may include carbon nanotubes grown substantially vertically to the first fabric layer 311 and the second fabric layer 312. The carbon nanotubes may have height of 30~40 μm. The carbon nanotubes may form carbon nanotube forest. The carbon nanotubes may include $RuO_2$ nanoparticles or $RuO_2$ layer formed on the surface.

The electrolyte layer 340 may be a gel type film.

FIGS. 17A to 17C illustrate a method for forming the supercapacitor of FIG. 16.

Referring to FIG. 17A, the first catalyst layer 321 and the first electrode layer 331 are formed on the first fabric layer 311. The first fabric layer 311 may be formed with conductive nylon fabric, conductive carbon fabric and so on.

The first catalyst layer 321 may be formed by stacking the aluminum (Al) layer and the iron (Fe) layer. The aluminum layer may be formed on the first fabric layer 311 using thermal deposition and the iron layer may be formed on the aluminum layer using e-beam deposition.

The first electrode layer 331 may be formed by growing carbon nanotubes to vertical direction on the first catalyst layer 321 and forming $RuO_2$ nanoparticles or a $RuO_2$ layer on the surface of the carbon nanotubes.

Referring to FIG. 17B, the second catalyst layer 322 and the second electrode layer 332 are formed on the second fabric layer 312. The second fabric layer 312 may be formed with conductive nylon fabric, conductive carbon fabric and so on.

The second catalyst layer 322 may be formed by stacking the aluminum (Al) layer and the iron (Fe) layer. The aluminum layer may be formed on the second fabric layer 312 using thermal deposition and the iron layer may be formed on the aluminum layer using e-beam deposition.

The second electrode layer 332 may be formed by growing carbon nanotubes to vertical direction on the second catalyst layer 322 and forming $RuO_2$ nanoparticles or a $RuO_2$ layer on the surface of the carbon nanotubes.

Referring to FIG. 17C, the electrolyte layer 340 is provided between the first electrode layer 331 and the second electrode layer 332. The electrolyte layer 340 may be formed to be a gel type film. The gel type film may be formed by method comprising adding polyvinyl alcohol (PVA) to DI water including $H_3PO_4$ to form a mixture, forming transparent solution by continuously stirring and heating the mixture in a mineral oil bath, and drying the solution in a Petri dish.

FIG. 18 illustrate a structure and electrochemical characteristics of a supercapacitor according to yet another embodiment of the present disclosure.

FIGS. 18a to 18d show a schematic illustration (top) and SEM (scanning electron microscopy) images (bottom) of the manufacturing procedure for forming a supercapacitor.

Referring to FIGS. 18a to 18d, single-wall carbon nanotubes are synthesized on a woven fabric of carbon fibers through chemical vapor deposition using an electron-beam-evaporated iron catalyst layer. The vertical growth of the carbon nanotubes forms a 30~40 μm high carbon nanotube forest that maximizes the surface area for the electrical double layer. $RuO_2$ nanoparticles are formed on the carbon nanotubes by electrochemical deposition.

Referring to FIG. 18e, the CV curves obtained at scan rates of between 5 and 100 mV/s reveal a quasi-rectangular shape of typical supercapacitors. Referring to FIG. 18f, from the Galvanostatic charge-discharge curves, the areal capacitances at current densities of 10, 5, 2, and 1 $mA/cm^2$ were calculated to be 74.6, 80.0, 85.2, and 87.9 $mF/cm^2$ respectively.

Referring to FIGS. 18g and 18h, since the gel electrolyte used was water-based, the potential window is limited to 0.8 V to prevent any damage being incurred by $H_2$ generation. Both the potential window (in series) and the total capacitance (in parallel) can be easily controlled by connecting multiple supercapacitors. Two supercapacitors in series or in parallel double either the potential limit or capacitance respectively compared to a single supercapacitor.

Referring to FIGS. 18i to 18l, the performance of the supercapacitor can remain unchanged up to 135° of bending, which is attributed to the high flexibility of its individual components. Only very minor variation is observed in the areal capacitance, even after four thousand charge-discharge cycles.

Example for Manufacturing a Stretchable Supercapacitor

A 10 nm thick Al layer was deposited on a carbon fabric using a thermal evaporator and a 3.5 nm thick Fe layer was deposited on the Al layer by an e-beam evaporator to form a catalyst. Carbon nanotubes (CNTs) was formed at atmospheric pressure by placing the catalyst-coated carbon fabric on a quartz plate, and then loading it into a 1 in diameter CVD quartz cylinder. The temperature was increased to 730° C. under a 100 sccm flow of 99.999% pure Ar and 50 sccm of Ar containing $H_2O$. When the target temperature was reached, 75 sccm of ethylene and 100 sccm of $H_2$ were introduced to the reactor for 10 min as the precursor and carrier gas respectively $RuO_2$ electroplating solution was prepared using 5 mM ruthenium(III) chloride hydrate, 0.1 M KCl, and 0.01 M HCl in DI water. 3M NaOH solution was slowly added until the pH of the plating solution reached 2.0. Prior to plating, the carbon nanotubes were hydrophilized by $O_2$ plasma using a reactive ion etcher. The plating solution was heated to 50° C. in a water bath and a cyclic voltammetry of between −0.2 V and 1.0 V was applied at a 0.05 mV/s scan rate using a potentiostat with a Pt counter electrode and an Ag/AgCl reference electrode in NaCl.

The electrolyte for the supercapacitor was prepared by adding 6 g of PVA (MW: 146000~186000 g/mol) to 60 mL of DI water containing 9 g of $H_3PO_4$. The resulting mixture was heated to 104° C. in a mineral oil bath with constant stirring until a transparent solution was obtained. The solution was poured into a Petri dish and dehydrated at room temperature to form a gel film A supercapacitor was formed by disposing $PVA/H_3PO_4$ between the carbon fabrics with $CNT/RuO_2$.

FIGS. 19A to 19E illustrate a wearable electronic device according to yet another embodiment of the present disclosure.

Referring to FIGS. 19A to 19E, a triboelectric generator and a Li-ion battery (stretchable power supply devices) are connected with a 3-axis accelerometer (fall detection sensor), a Bluetooth (wireless communication unit), and a microcontroller through conductive carbon fibers (conductive threads) on clothes such as a jacket. The triboelectric generator may comprise a first triboelectric generation part and a second triboelectric generation part. The first triboelectric generation part and the second triboelectric generation part may comprise a conductive nylon layer coated with materials having different work function (large work function gap) such as PEIE and silicone rubber. The second triboelectric generation part may be worn on the wrist and the first triboelectric generation part may be equipped on the sleeve corresponding to the second triboelectric generation part. The Li-ion battery may be worn on the wrist or equipped on clothes near to the first triboelectric generation part. The accelerometer, the Bluetooth, and the microcontroller may be disposed on the chest region. The contact/release friction between the first triboelectric generation part and the second triboelectric generation part during arm movements in walking or running generates electricity. The power (electricity) generated by the triboelectric generator is transferred via conductive threads to a rectifier and then the Li-ion battery. The rectifier is disposed between the triboelectric generator and the Li-ion battery and converts the generated alternating current (AC) into the direct current (DC) to charge the Li-ion battery. The Li-ion battery provide the charged power to the 3-axis accelerometer, the Bluetooth, and the microcontroller. Output voltage changes from the accelerometer due to accelerations into x, y, z directions are transmitted to the microcontroller. The software embedded in the microcontroller calculates the vector sum of 3-axis accelerations and sends fall detection data to external devices via Bluetooth. FIG. 19C illustrates operating mechanism of the wearable electronic device and FIG. 19D illustrates circuit diagram of the wearable electronic device.

This embodiment describes the wearable fall detection system as an example of the wearable electronic device, but the present disclosure is not limited to the wearable fall detection system. The wearable electronic device may comprise one or more sensors sensing various vital signs, bio signals, and/or body's movement changes.

FIGS. 20A to 20D illustrate application examples of the wearable electronic device of FIG. 19A.

Referring to FIG. 20A, to verify the output signals from the 3-axis accelerometer, a subject quickly moved the 3-axis accelerometer from origin coordinate (0,0,0) to the designated coordinate (1,2,−2). Due to positive moving along x and y directions, the signals representing acceleration towards both directions showed the positive peaks at the moment of acceleration (black and red plots). On the other hand, the signals representing acceleration towards z direction showed the negative peaks at the same moment because of the device's movement towards negative z direction (blue plots). The values of vector sum are calculated by the microcontroller using the acceleration values of each direction (purple plots).

Referring to FIG. 20B, the subject wore the jacket equipped with the fall detection system and performed various motions. While doing so, the signals of the vector sum were calculated in real time and simultaneously transferred to the external computer via the Bluetooth. The simple motions of sitting down and standing up induced a low single valley of the vector sum (black and red plots). The continuous motions of walking and stepping up/down the stairs generated low and multiple peaks/valleys of the vector sum (blue and pink/dark plots) while running induced multiple and relatively larger peaks/valleys of the vector sum (dark blue plots). On the other hand, the motion of falling down showed the largest peaks/valleys of the vector sum (purple plots).

Referring to FIG. 20C, in contrast to other motions, the falling motion induced distinctive signals. When the subject falls down, there should be a short period of free fall before the subject hits the ground. The free fall could be detected by observing a gradual increase of the slope of the vector sum (dotted black circle). Once the free fall ended, the large impact signal was followed. Lastly, the value of the vector sum remains unchanged after the large impact signal due to movelessness of the fallen patient (dotted red oval).

Referring to FIG. 20D, using the distinctive signal characteristics of the falling motion, the fall detection system could recognize whether the wearer fell or not. Once the free fall took place, a large impact and a span of motionlessness were detected successively. Then, the fall detection system may send emergency signal (distress signal) to emergency center (rescue center) via external device such as computer or smartphone FIG. 21 illustrates a structure and motion principle of a wearable electronic device according to yet another embodiment of the present disclosure. The wearable electronic device is manufactured on a conductive carbon fabric and the conductive carbon fabric allows the wearable electronic device to be woven onto designated locations of clothes and interconnected by conductive threads.

Referring to FIG. 21a, the triboelectric generator (TEG) may be disposed in the armpit region to maximize friction whereas the supercapacitor may be disposed on the chest region safe from friction damage and close to the triboelectric generator. Electricity may be generated by the typical swinging motion during walking and stored.

FIG. 21b shows a circuit diagram of the integrated electronic devices. Multiple triboelectric generators (TEG) are connected in parallel to generate sufficient electrical current to charge the supercapacitor (SC). The rectifier disposed between the triboelectric generator (TEG) and the supercapacitor (SC) converts the generated alternating current (AC) into the direct current (DC) to charge the supercapacitor (SC).

Referring to FIGS. 21c to 21e, the design of the triboelectric generator (TEG) is based on a controlled alignment of four complementary materials, which allows them to utilize both the vertical and horizontal frictions generated between the arm and the torso. For the inner arm, polyurethane (PU, quadratic mean roughness (Rq)=158 nm) and polyimide (PI, Rq=23.5 nm) are alternatingly patterned on carbon fabric to form the first triboelectric generation part (TEG I). On the opposite surface, polydimethylsiloxane (PDMS, Rq=49.4 nm) and aluminum (Al, Rq=200 nm) are alternatingly patterned on carbon fabric to form the second triboelectric generation part (TEG II). Each of these materials has its own relative degree of triboelectric polarity, with Al connected to the circuit as a conducting material which transfers electrons to the polymer surfaces. The generated electricity is stored in the integrated fabric based supercapacitor (SC) The supercapacitor (SC) has a structure in which carbon fabric, carbon nanotube (CNT)/$RuO_2$ electrode, polyvinyl alcohol (PVA)/$H_3PO_4$ gel electrolyte, CNT/$RuO_2$, and carbon fabric are stacked.

FIG. 22 illustrates demonstration and measurement of electrical signals of the wearable electronic device of FIG. 21.

Referring to FIG. 22a, the fabric based triboelectric generator (TEG) (5 cm×9 cm, 18 lines) and the supercapacitor (SC) are easily sewn into clothes such as a shirt and then connected by conductive carbon threads.

Referring to FIGS. 22b and 22c, the energy harvest through regular daily activities such as running and walking was simulated by rubbing the triboelectric generator (TEG) at various speeds. At a speed of 1.5 Hz, the average output voltage and the rectified current were measured as 33 V and 0.25 µA respectively. The generated electricity stored in the supercapacitor was powerful enough to light up a LED.

Referring to FIG. 22d, the frequency of rubbing determines the slope of charge accumulation, exhibiting a proportional relationship within a range of 0.67~4 Hz. This allows the device to function as a wearable self-powered human activity monitor.

FIG. 22e shows the rectified output current (black, left axis) and the charge accumulation (red, right axis) recorded from a subject simulating normal jogging procedure of stretching, walking, running, sprinting, and a cool-down walk. Thus, if the slope of the charge accumulation is monitored, the activity of the subject wearing the wearable electronic device can be tracked. The slope associated with stretching, walking, running, sprinting, and cool-down are 0.48, 8.4, 22, 53, and 9.6 nC/s respectively.

FIG. 22f shows voltage versus time plots of three different capacitors with capacitances of 1, 10 and 100 nF. Although a fast charging/discharging capacitor (1 nF) offers the better sensitivity for human activity monitoring, a high capacitance capacitor (100 nF) is well suited to long-term monitoring.

Referring to FIGS. 22g and 22h, the supercapacitor charged by the triboelectric generator can supply power to other sensors. For example, the supercapacitor charged by the triboelectric generator can provide the necessary current to a pressure sensor. The pressure sensor consists of a porous pressure sensitive rubber sandwiched between carbon fabrics.

Referring to FIGS. 22i and 22j, the resistance of the porous pressure sensitive rubber changes linearly with applied pressure.

Referring to FIG. 22k, by measuring the change in current, it is possible to determine the applied pressure. This is demonstrated by placing 20, 50, 100 and 200 g weights on the sensor.

Although the preferred embodiments of the present disclosure have been disclosed for illustrative purposes, those skilled in the art will appreciate that various modifications, additions and substitutions are possible without departing from the scope and spirit of the disclosure as disclosed in the accompanying claims.

What is claimed is:

1. A stretchable triboelectric generator, comprising:
    a first stretchable triboelectric generation part comprising a first fabric layer and a first friction layer on the first fabric layer; and
    a second stretchable triboelectric generation part comprising a second fabric layer and a second friction layer on the second fabric layer,
    wherein the first friction layer comprises first friction patterns and second friction patterns disposed alternatingly, and the second friction layer comprises third friction patterns and fourth friction patterns disposed alternatingly.

2. The stretchable triboelectric generator of claim 1, wherein a work function of the first friction layer is different from a work function of the second friction layer.

3. The stretchable triboelectric generator of claim 1, wherein a charge amount by triboelectrification of the first friction layer and the second friction layer is determined by a difference between a work function of the first friction layer and that of the second friction layer.

4. The stretchable triboelectric generator of claim 1, wherein the first friction layer comprises PEIE and the second friction layer comprises silicone rubber.

5. The stretchable triboelectric generator of claim 1, wherein the first friction patterns, the second friction patterns, the third friction patterns, and the fourth friction patterns have different surface roughnesses.

6. The stretchable triboelectric generator of claim 1, wherein the first friction patterns comprise polyurethane, the second friction patterns comprise polyimide, the third friction patterns comprise polydimethylsiloxane, and the fourth friction patterns comprise aluminum (Al).

7. The stretchable triboelectric generator of claim 1, wherein the first friction patterns and the second friction patterns have substantially the same thickness, and the third friction patterns and the fourth friction patterns have substantially the same thickness.

8. The stretchable triboelectric generator of claim 1, wherein the first fabric layer and the second fabric layer comprise at least one of conductive nylon fabric or conductive carbon fabric.

\* \* \* \* \*